(12) United States Patent
Konduru et al.

(10) Patent No.: US 11,566,218 B2
(45) Date of Patent: Jan. 31, 2023

(54) APPARATUS AND METHODS FOR ADJUSTABLE VOLUME CELL CULTURE

(71) Applicant: Global Life Sciences Solutions USA LLC, Marlborough, MA (US)

(72) Inventors: Nagaraju Konduru, Bangalore Karnataka (IN); Manoj Ramakrishna, Bangalore Karnataka (IN); Haresh Digambar Patil, Bangalore Karnataka (IN)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 266 days.

(21) Appl. No.: 16/314,906

(22) PCT Filed: Jun. 22, 2017

(86) PCT No.: PCT/EP2017/065349
§ 371 (c)(1),
(2) Date: Jan. 3, 2019

(87) PCT Pub. No.: WO2018/007157
PCT Pub. Date: Jan. 11, 2018

(65) Prior Publication Data
US 2019/0309254 A1    Oct. 10, 2019

(30) Foreign Application Priority Data
Jul. 5, 2016   (IN) .............................. 201611023094

(51) Int. Cl.
*C12M 1/34* (2006.01)
*C12M 1/12* (2006.01)
(Continued)

(52) U.S. Cl.
CPC ............ *C12M 41/44* (2013.01); *C12M 23/06* (2013.01); *C12M 23/14* (2013.01); *C12M 23/26* (2013.01);
(Continued)

(58) Field of Classification Search
CPC ...... C12M 23/06; C12M 23/14; C12M 23/26; C12M 23/46; C12M 23/48; C12M 27/16; C12M 41/44; C12M 41/48
See application file for complete search history.

(56) References Cited

U.S. PATENT DOCUMENTS

2003/0143727 A1    7/2003  Chang
2007/0037276 A1*   2/2007  De Crecy ................ C12N 5/04
                                              435/293.1
(Continued)

FOREIGN PATENT DOCUMENTS

JP      2012-120495 A    6/2012
WO      1990/10690 A1    9/1990
(Continued)

OTHER PUBLICATIONS

PCT International Search Report and Written Opinion for PCT Application No. PCT/EP2017/065349 dated Nov. 27, 2017 (18 pages).
(Continued)

*Primary Examiner* — Lydia Edwards
(74) *Attorney, Agent, or Firm* — Eversheds Sutherland (US) LLP

(57) ABSTRACT

Cell culture apparatus is disclosed comprising: a cell culture container comprising a flexible tube; a support table; and a pair of opposed holders for holding opposed portions of the tube in a fluid tight manner such that fluid cannot pass through the respective portion inside the tube, the spacing between the said pair being adjustable to provide an adjustable sealed volume in the tube between the holder pair.

12 Claims, 11 Drawing Sheets

(51) Int. Cl.
*C12M 1/00* (2006.01)
*C12M 3/00* (2006.01)
*C12M 3/06* (2006.01)
*C12M 1/36* (2006.01)

(52) U.S. Cl.
CPC ............ *C12M 23/46* (2013.01); *C12M 23/48* (2013.01); *C12M 27/16* (2013.01); *C12M 41/48* (2013.01)

(56) References Cited

U.S. PATENT DOCUMENTS

2013/0157353 A1\* 6/2013 Dijkhuizen Borgart .................... C12M 23/14 435/297.2
2016/0152935 A1\* 6/2016 Roosloot ................ C12M 29/10 435/297.1

FOREIGN PATENT DOCUMENTS

| WO | 2005/079560 A1 | 9/2005 |
| WO | 2008/013967 A2 | 1/2008 |
| WO | 2009/123173 A1 | 10/2009 |
| WO | 2013/114859 A1 | 8/2013 |
| WO | 2015/009153 A1 | 1/2015 |
| WO | 2015/180908 A1 | 12/2015 |

OTHER PUBLICATIONS

Japanese Office Action for JP Application No. 2018-567577 dated Apr. 12, 2021 (6 pages with English translation).
Eibl et al., "Disposable Bioreactors for Plant Liquid Cultures at Litre-Scale," Eng. Life Sci., 2009, 9*3):156-164.
Sekine et al., "Simple and Effective Method to Produce Monoclonal Antibodies Using Cultures Bags," Journal of the Society for Biotechnology, 2009, 87(9):437-441.

\* cited by examiner

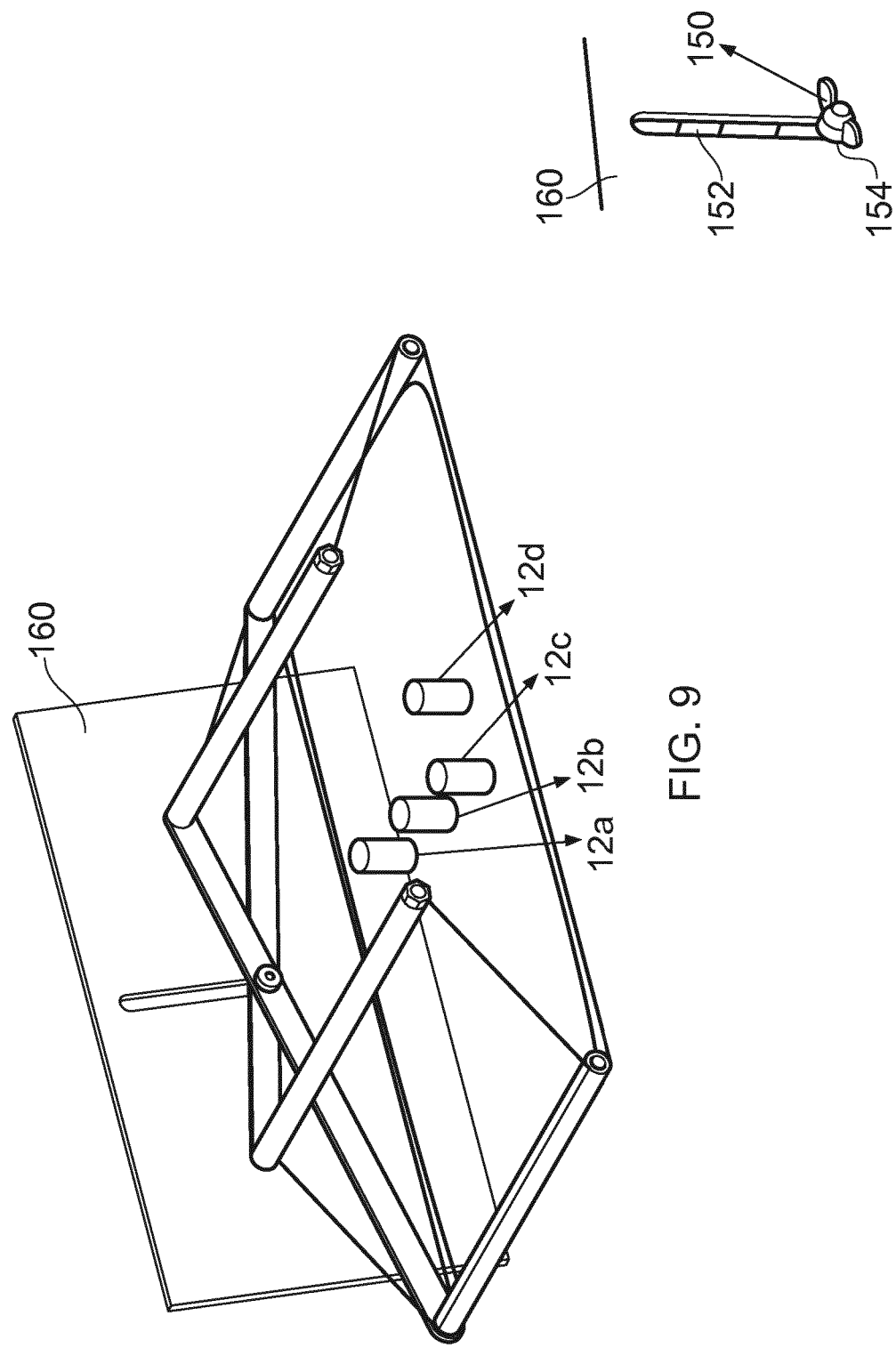

APPARATUS AND METHODS FOR ADJUSTABLE VOLUME CELL CULTURE

CROSS REFERENCE TO RELATED APPLICATIONS

This application claims the priority benefit of PCT/EP2017/065349 filed on Jun. 22, 2017 which claims priority benefit of Indian Application No. 201611023094, filed Jul. 5, 2016. The entire contents of which are hereby incorporated by reference herein.

FIELD OF THE INVENTION

The present invention relates to apparatus and methods for variable volume ex-vivo cell culture, in particular for optimising said culture.

BACKGROUND OF THE INVENTION

Conventional cell culturing involves expanding cells into larger and larger volume containers to keep space with the increasing quantities of cells. This stepwise approach usually takes the form of initial expansion of the cell of interest from a small sample in a vial, typically of just a few millilitres, to large volumes (e.g., 500-2000 L) in cell bags or tanks. During the cell expansion phase, the cells are initially inoculated into flasks or spinner bottles to revive cell lines. Later cells will be transferred and expanded in the cell bags on a rocker or in stirred tanks. In the expansion process gradually the cells are transferred to the next bigger sized flask/spinner bottle/cell bag/tank and expansion is continued. There are challenges in using a large container with a small population of cells, i.e. the amount of costly cell culture media required is out of proportion to the return of cells produced; and dead spaces can occur where no or few cells are present.

A cell culture container of variable volume would address some of the challenges mentioned above, and has been proposed in WO2015/009153, and a similar disclosure is made in US20130157353. In these documents, a cell culture bag is shown which lies on a table. A roller is pressed against the table to squeeze the whole width of the bag. Movement of the roller relative to the bag allows the bag to obtain more volume. However, the inventors have realised that these known variable volume cell culture bags have further challenges, i.e. holding and managing a large container size during initial small volume culture; preventing any unused area of the container from coming into contact with the cell culture during initial small volume culture; increasing volume without interfering with inlet and outlet ports of the container; and controlling the increasing volume thereby to optimise cell container volume throughout the cell expansion phase.

SUMMARY OF THE INVENTION

The object of the present invention is to provide cell culture apparatus which includes embodiments that address the challenges mentioned above in regard to the known cell culture bags identified above.

According to a first aspect of the invention, there is provided cell culture apparatus comprising: a cell culture container comprising a flexible tube; a support table; and a pair of opposed holders for holding opposed portions of the tube in a fluid tight manner such that fluid cannot pass through the respective portion inside the tube, the spacing between the said pair being adjustable to provide an adjustable sealed volume in the tube between the holder pair. In that first aspect, the holder pair provide a positive securement at each end of the tube and simultaneously allow adjustable volume.

Preferably, the culture container includes plural fluid ports located between the holder pair when the container is mounted on the table. Thereby, as the holders move apart when more volume is required, that movement does not interfere with the ports and their respective fluid communications.

Preferably the flexible tube is folded or rolled at least once at the holder. Thereby, the compressive forces needed to provide a fluid tight seal at the holders are reduced because the tube material is folded, not just compressed at the holders.

Preferably the apparatus is controlled using a feedback mechanism to provide accurate position adjustment and thereby better control of the volume between the holders.

According to a second aspect, the invention comprises a cell culture container formed from a tube of polymeric material, initially laid flat then folded or rolled at at least one end of the tube, having access ports in a portion of the tube which is unfolded or unrolled. Preferably, both ends of the tube are folded or rolled on each side of side access ports. Thereby, the tube can be unfolded or unrolled to increase the available cell culture volume within the tube as it is filled with fluid.

According to yet another aspect of the invention, there is provided a method for providing a variable volume in a cell culture, the method comprising the steps of:

providing a cell culture container initially in the form of a tube laid flat; sealing a central portion of the tube at either side of said central portion by mechanical compression of the tube and optionally by folding of the tube;

introducing liquids for cell culture into the central portion leaving opposed ends of the tube substantially free of said liquids, as a result of said sealing;

moving the position of said compression/folding in opposed directions to increase the size of the central portion and thereby to increased cell culture volume.

Other aspects of the invention are envisaged. Thus, the recitation of a feature in a claim is not intended to limit that feature to its combination with all other features in that claim, rather, where the context permits, such a feature may be combined with other features found in other claims or found in the description to provide other aspects of the invention. In keeping, more advantages and benefits of those other aspects of the present invention will be readily apparent to the person skilled in the art, in particular, in view of the detailed description below.

DRAWINGS

The invention will now be described in more detail with reference to the appended drawings, wherein.

Figure 4:
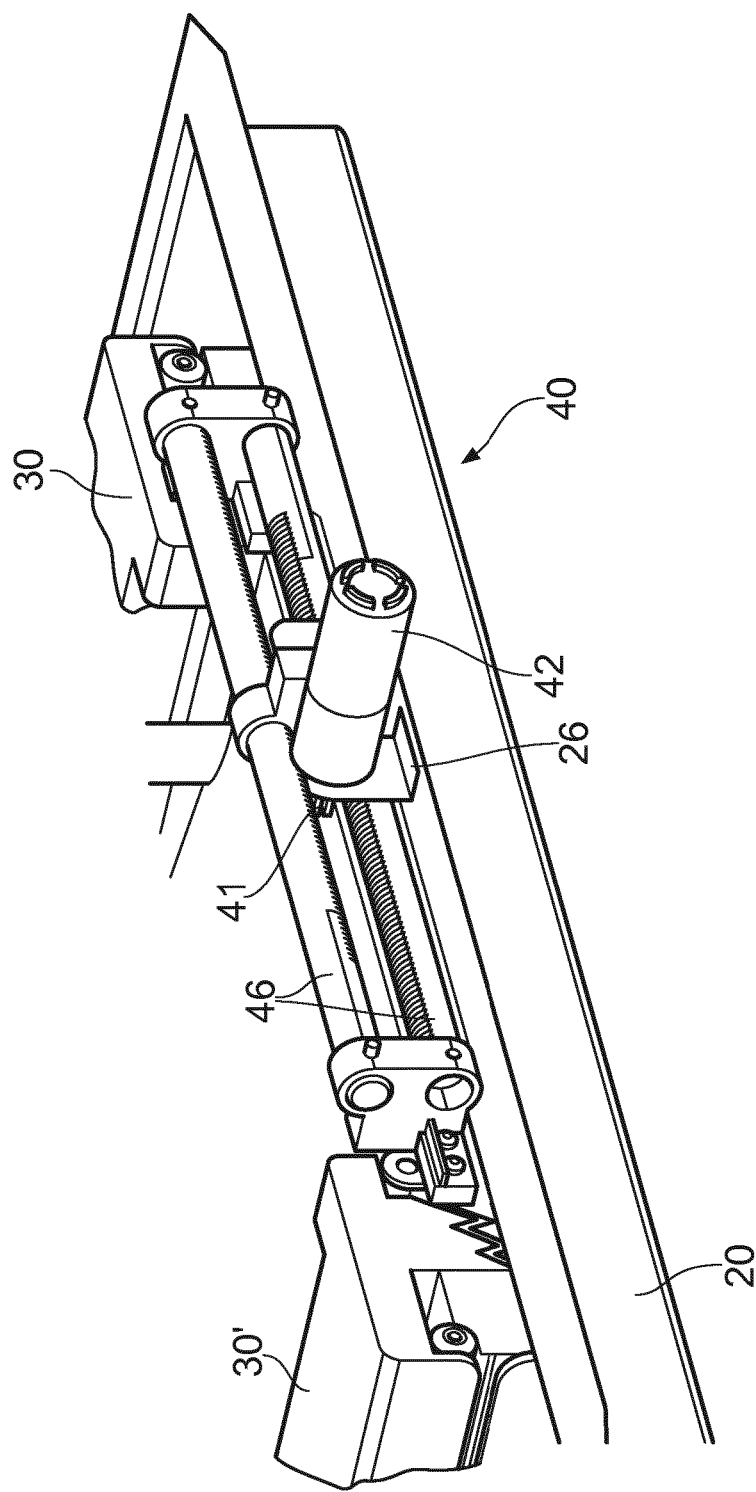
Figure 5:
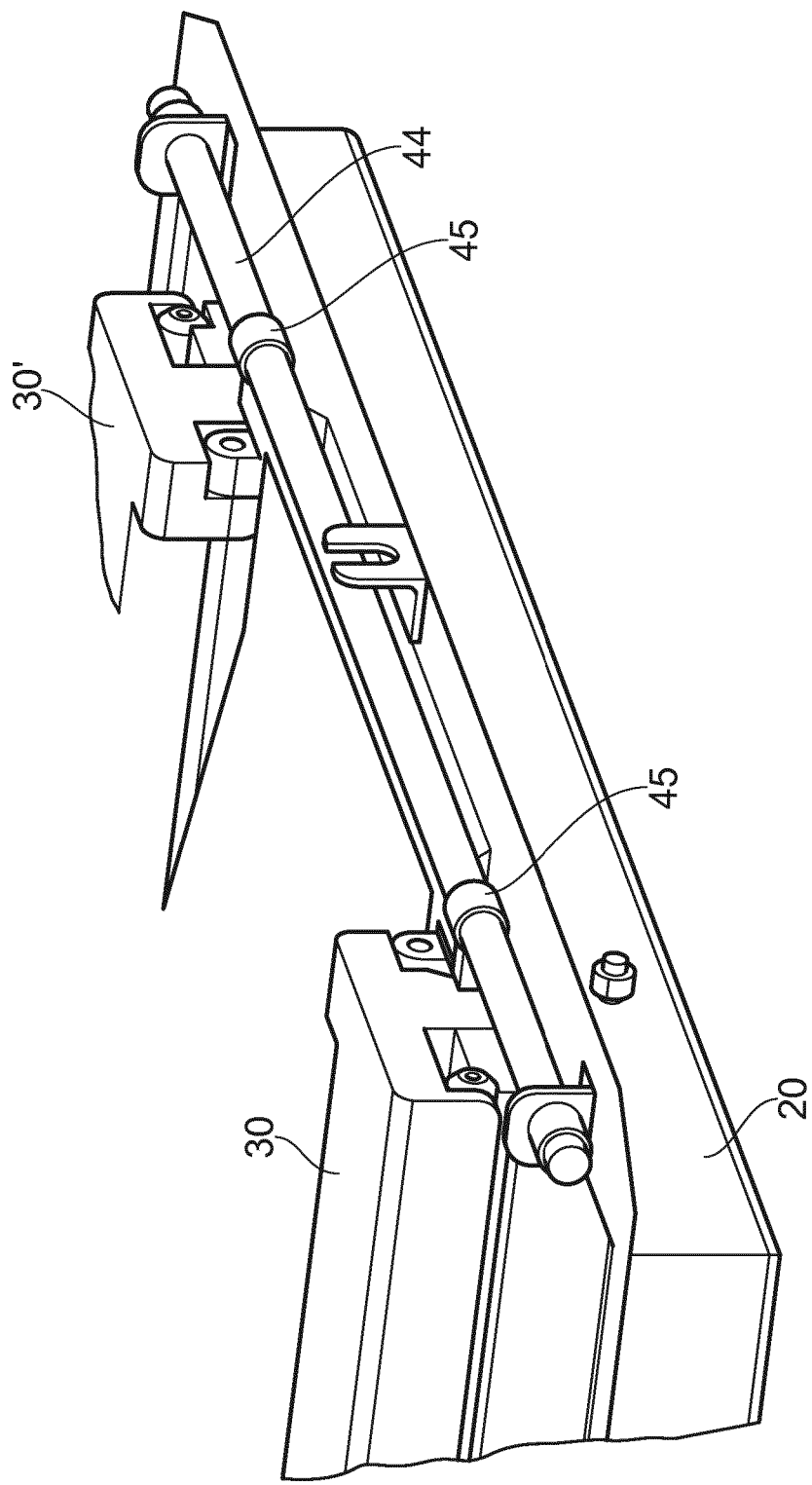
Figure 6:
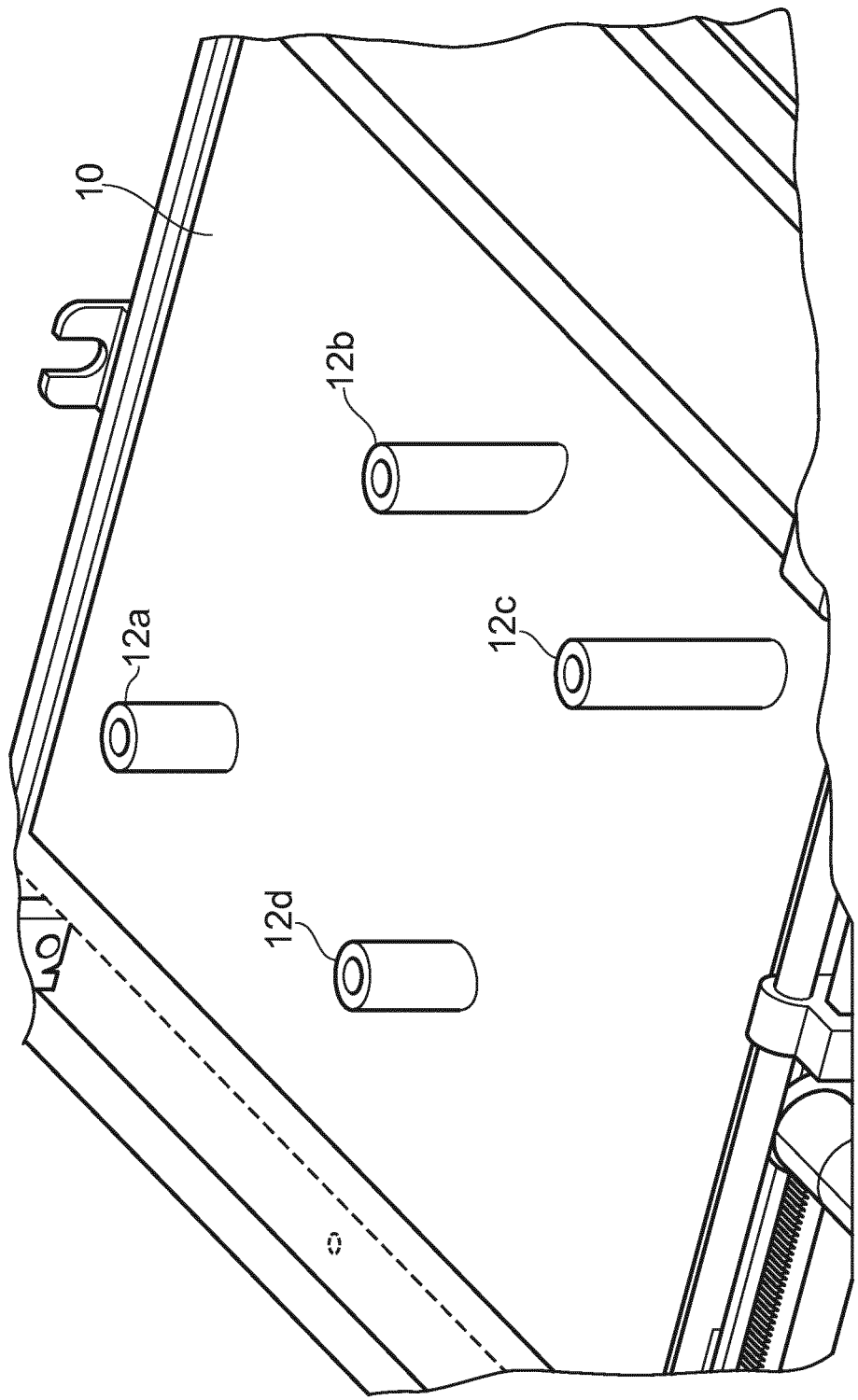
Figure 7:
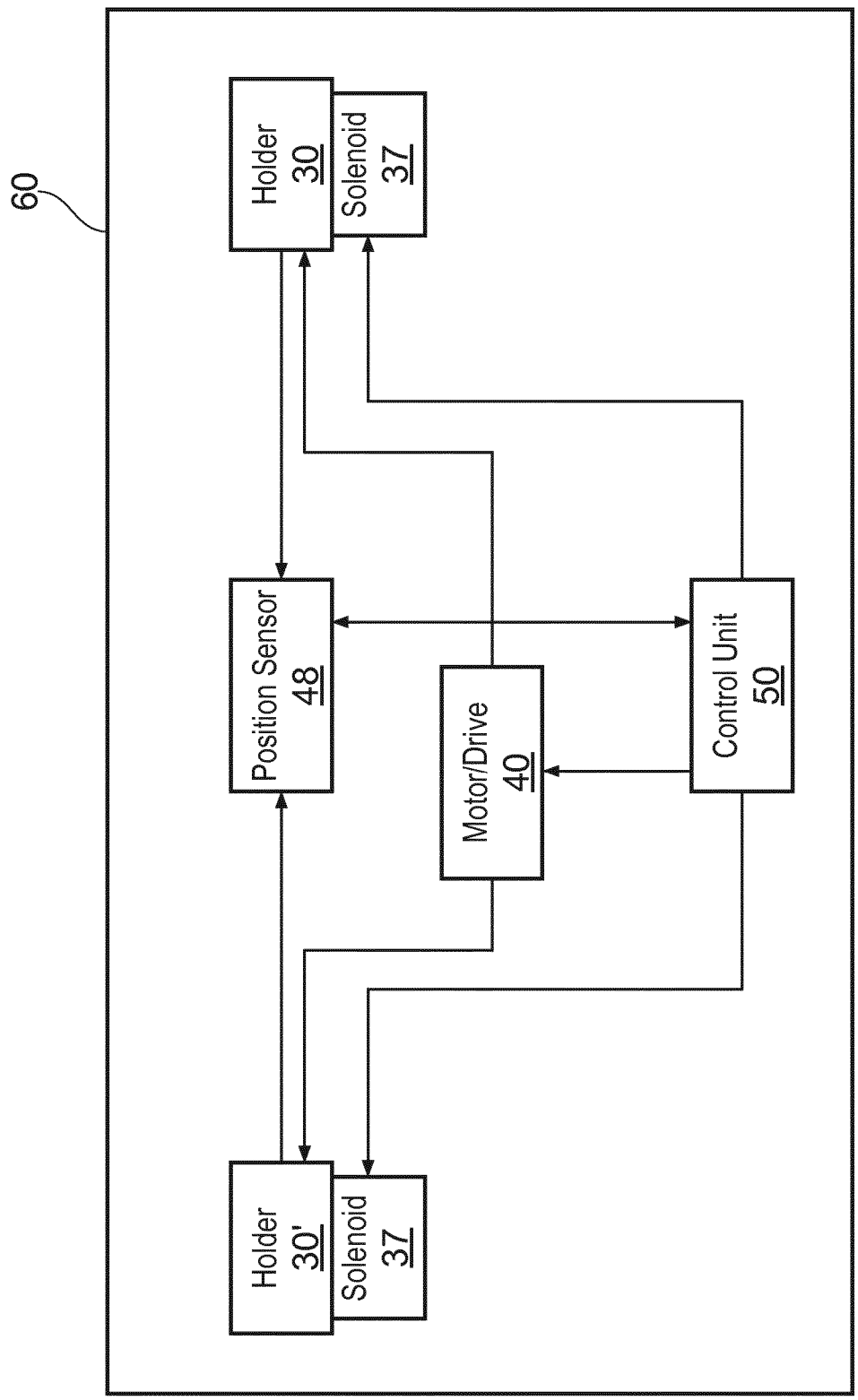

FIGS. 4, 5 and 6 each show a partial view of features of the first embodiment;

FIG. 7 shows a schematic representation of a control circuit for the first embodiment; and FIGS. 8 to 14 show a second embodiment of a cell culture apparatus.

DETAILED DESCRIPTION

Figure 1:
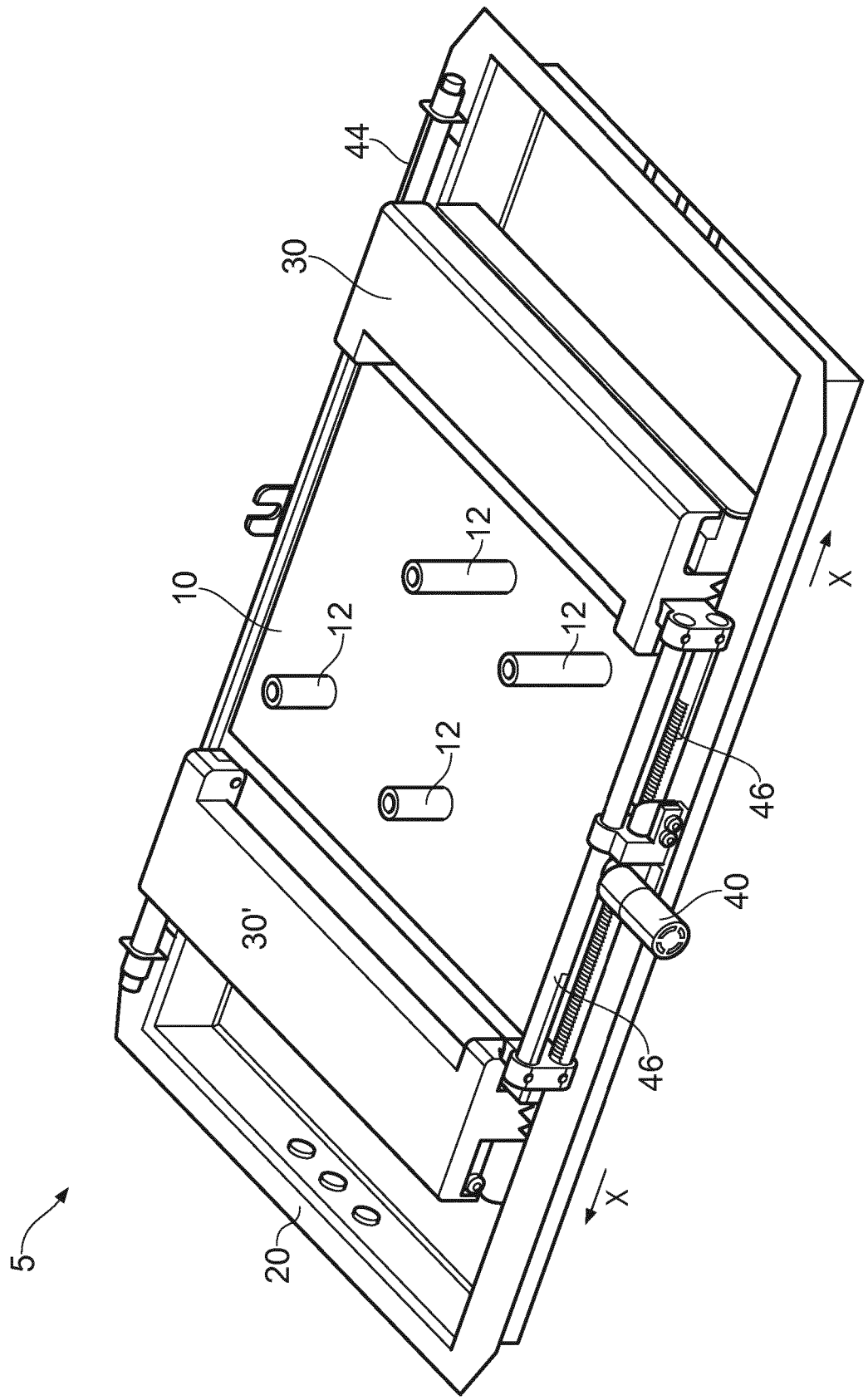
FIG. 1 shows a pictorial view of one embodiment of a cell culture apparatus.

FIG. 1 shows a variable volume cell culture apparatus 5 including a cell culture bag or container, in this case, in the form of a cell culture tube 10, laid flat on support table 22 in turn supported on a rockable support tray 20. The tube 10 is formed from a polymer as an elongate seemless tube where opposite sides are bought together to form a double layered closed expandable cell culture tube. The tube 10 further includes access ports 12, which permit fluid and gas entry into and egress from the inside of the tube, thus providing a cell culture container around the ports.

Respective opposed ends of the tube 10 are held, folded, inside opposed tube holders 30 and 30' which holders are moveable by means of a holder moving mechanism 40. Thereby, since the space between the holders can be adjusted, then it follows that the volume of the cell culture container too can be adjusted. The minimum volume required for starting cell culture is shown in FIG. 1.

Figure 2:
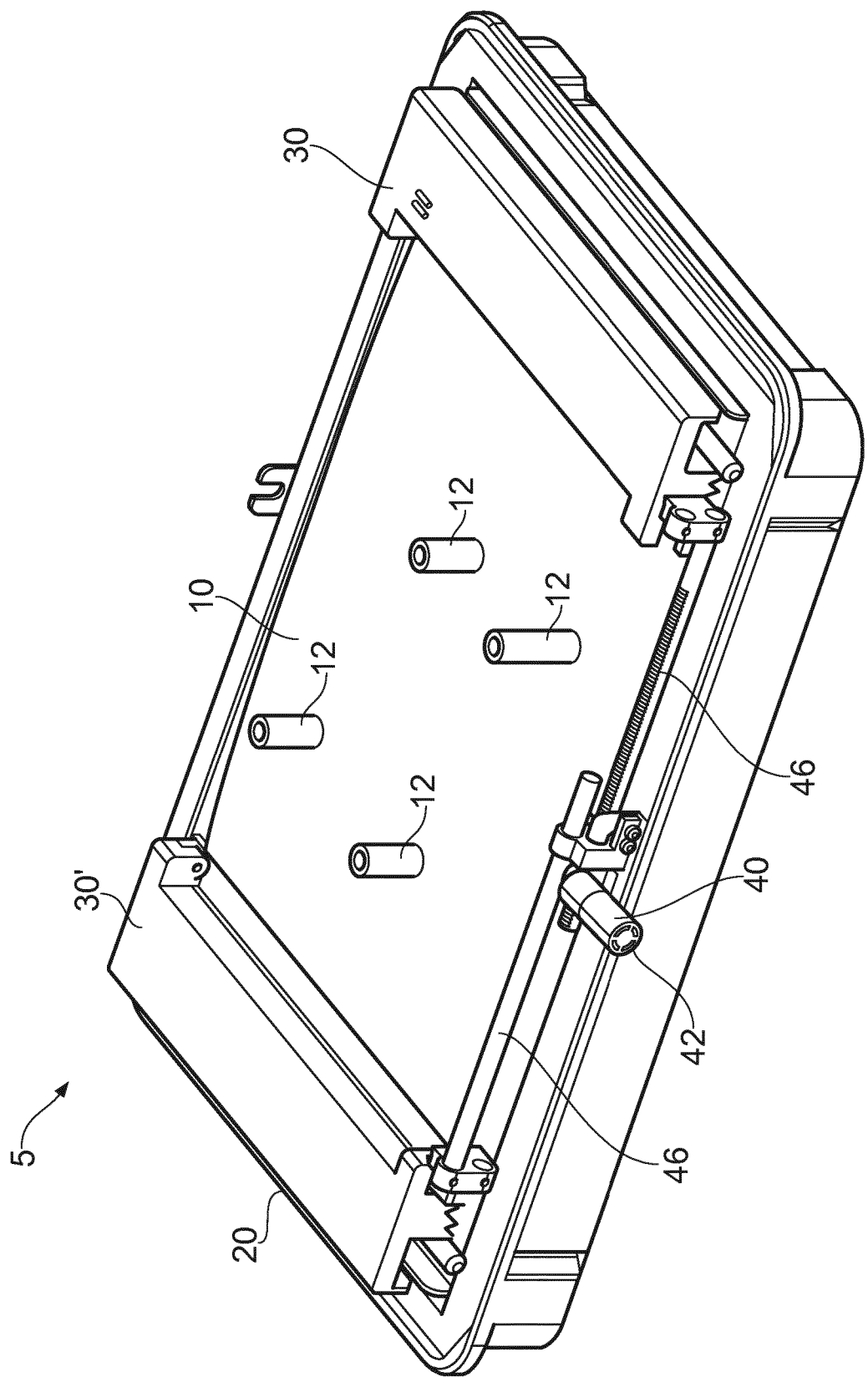
FIG. 2 shows the first embodiment but with the apparatus in a different configuration compared to FIG. 1.

Referring additionally to FIG. 2, the holders 30 and 30' are shown moved apart to provide more volume for cell culture in the now larger tube portion 10 that exists between the holders 30 and 30'. To facilitate the higher volume, the holders 30 and 30' are synchronously moved, as described below, so that equal amounts of the tube are unfolded from both sides. This can be done as a slow continuous movement or, as in this embodiment, in a stepped movement by employing a stepper motor 42. The holders can be moved apart until the desired cell culture volume is obtained, based on the distance between the holders. The holders are held in place by guides, for example a tubular guide rail 44, which allows linear translation in the direction of arrows X, and, generally after completion of a cell culture process, translation is the opposite direction to return to a position where an initial small volume is required, i.e. as shown in FIG. 1. The translation is effected, in this embodiment by the stepper motor 42 which is fixed in a central position and rotates a fixed axis pinion. The fixed axis pinion in turn causes the translational movement of a pair of toothed racks meshed with the top and bottom teeth respectively of the pinion. Rotation of the pinion causes opposing movement of the two racks.

Figure 3:
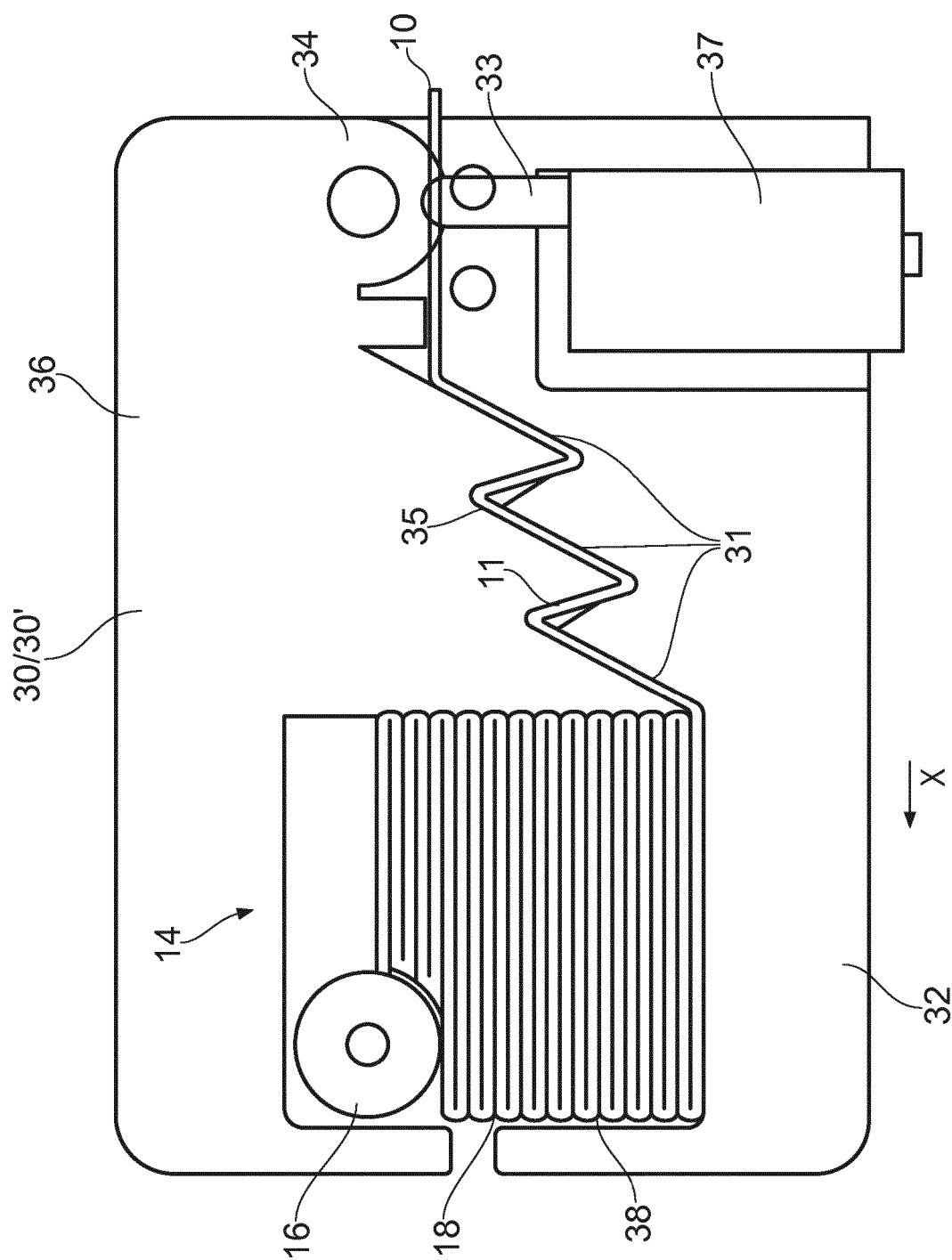
FIG. 3 shows a sectional view of features of the first embodiment.

FIG. 3 shows a cross sectional view of holder 30, holder 30' being a mirror image of the holder 30 shown. The holder 30 includes a fixed lower jaw 32 connected by a loosely fitting hinge pin 34 to an upper moveable jaw 36. In use the jaws 32 and 36 are urged together, for example by a tension spring and can be forced apart for loading a tube 10 by an electrically operated actuator 37 mounted to the lower jaw 32 which includes a release pin 33 which pushes against the upper jaw 36 to increase the gap between the two jaws. The jaws 32 and 36 further include complementary teeth 31 which come together closely, but do not touch, and form a circuitous path 35 between them, thereby, effectively folding the tube by more than 90 degrees to increase the sealing action of the teeth. An end portion 14 of the tube 10 is fitted between the jaws 32/36 such that an end stop rod 16 and a folded and pleated portion 18 of the end 14 are held in place in a cavity 38 formed between the jaws, and a further clamped portion 11 of the end 14 is held between the teeth 31 in the path 35. In use, sufficient clamping force is exerted by the teeth 31 to keep the tube 10 fluid tight at the clamped portion 11, but the tube can still be pulled through the circuitous path 35 when the holders 30/30' are moved in the direction of arrow X. The jaws 31 are over-molded with an elastomer to provide a sealing grip on the tube, but to allow sliding of the tube 10 relative to the jaws when needed.

FIG. 4 shows the holder drive mechanism 40 in more detail. In particular, the stepper motor 42 and its drive pinion 41 mentioned above can be seen in this view, mounted in fixed relation to the tray 20 by a mounting plate 26. The pinion's teeth cooperate with the teeth of respective racks 46 which are each fixed to one of the lower jaws 32 of a respective holder 30/30'. As described above, rotation of the pinion causes each rack, and consequently, each holder to move apart, or together synchronously by equal amounts.

FIG. 5 shows the rear face of the tray 20, including a guide rail 44 fixed to the tray 20 and guide bushes 45 encircling the rail 44 which are attached to each lower jaw 32 of a respective holder 30/30' and are moved along the guide rail 44 when the holders 30/30' are driven by the drive mechanism 40.

FIG. 6 shows the arrangement of central ports in more detail, including a liquid feed port 12a; a harvesting port 12b; a sample collection port 12c; and a gas feed port 12d.

FIG. 7 shows a schematic representation of the control circuit 60 for the hardware described above, and includes a position sensor 48, for example a linear encoder with components mounted to the rail 44, which senses the position of the two holders. Included also is a control unit 50 which takes information from the position sensor 48 to determine the dimension between the holders 30/30', and sends command signals to the drive mechanism 40 to adjust the position of the holders, according to, in this instance, a predetermined cell culture protocol which can be altered to suit the cell density determined from samples taken from the cell sample port 12c. feedback from the sensor can be detected by the control unit to stop the drive mechanism at the desired position.

The above embodiment has the advantages of: the holders 30/30' hold the tube in position and stored the unused area of tube to keep it secure and out of the way until needed during cell culture; the two holders move synchronously away from each other to control bag volume throughout cell expansion thus providing optimal cell culture volume but holding both ends of the tube securely; symmetrical unbundling of tube at either side while the tube ports remain in a relatively stationary position; and the apparatus can be made fully automated. It will be appreciated that the unused portions 14 of the tube 10 could be stored in a different manner, for example rolled, instead of folded.

Figure 8:
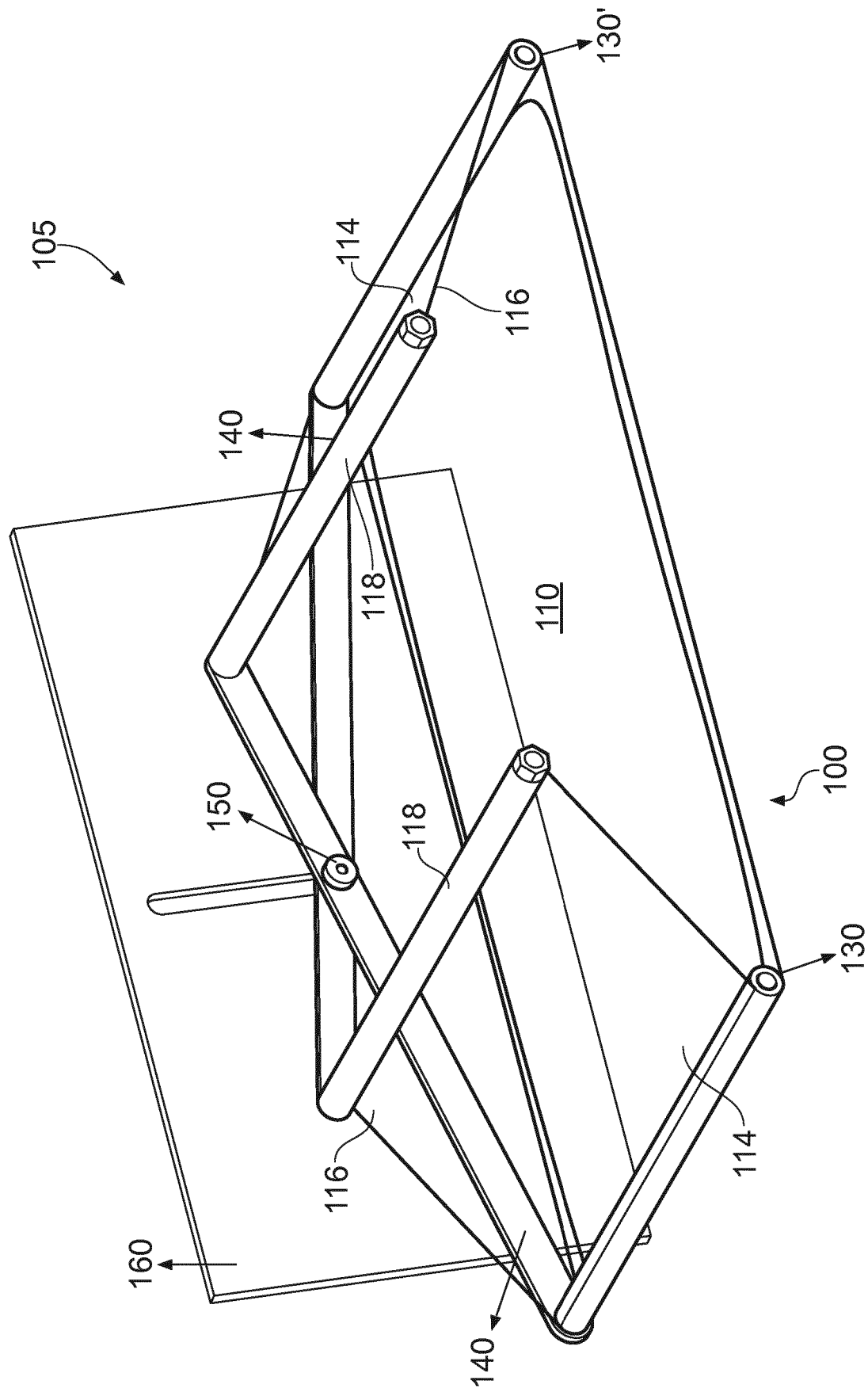

FIGS. 8 to 14 show views of a second embodiment 105 of the invention which is simpler than the first embodiment but requires manual adjustment to provide cell culture volume adjustment. FIG. 8 shows a cell culture tube 100 initially laid flat, including a central area 100 which will contain cell culture liquid in use, and side areas 114 which are sealed fluid tight from the central area by virtue of the sealing compressive forces exerted by a pair of rollers 130 and 130' which react against the tension in the tube portion 110. The rollers effectively fold the tube by more than 90 degrees to further increase their sealing effect. Ends 116 of the tube 100 are held at stop ends 118. The stop ends 118 and an opposing roller 130/130' are connected as a pair by a scissor action frame which has an adjustable pivot point 150. Adjustment of the pivot point 150 moves the rollers 130/130' apart, and brings the associated stop end 118 closer to the roller 130/130', resulting in a greater dimension between the two rollers 130/130' and so more cell culture volume at the central portion 110.

FIGS. 9 and 10 show more details of the apparatus shown in FIG. 8. In FIG. 9, centrally positioned ports 12*a*, *b c* and *d* are illustrated corresponding the ports described above. FIG. 10 shows more detail of the adjustment mechanism, which in this case comprises a simple slot 152 in a back plate 160 and a bolt and wing nut 154 which can be tightened in any position in the slot to hold the frame 140 in the desired position.

Figure 12:
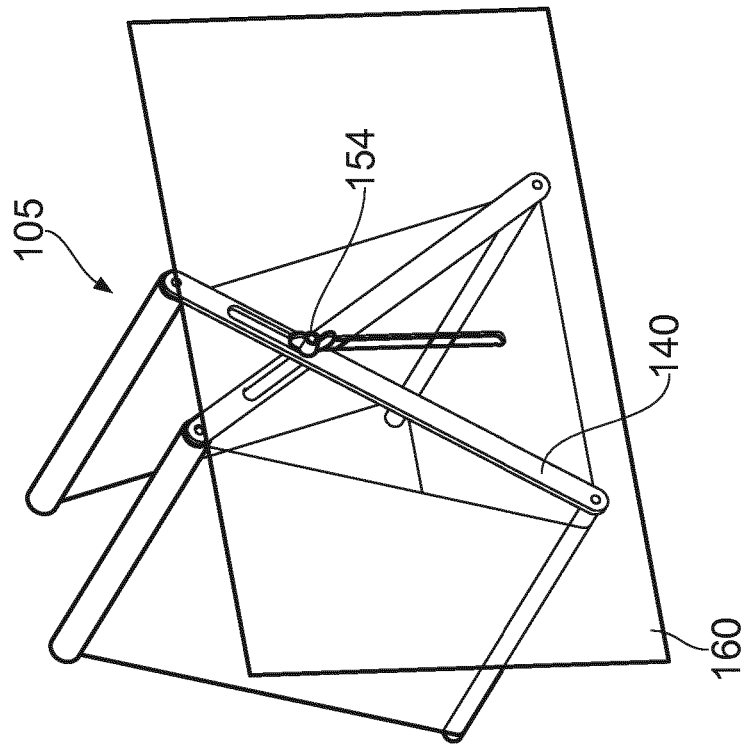
Figure 11:
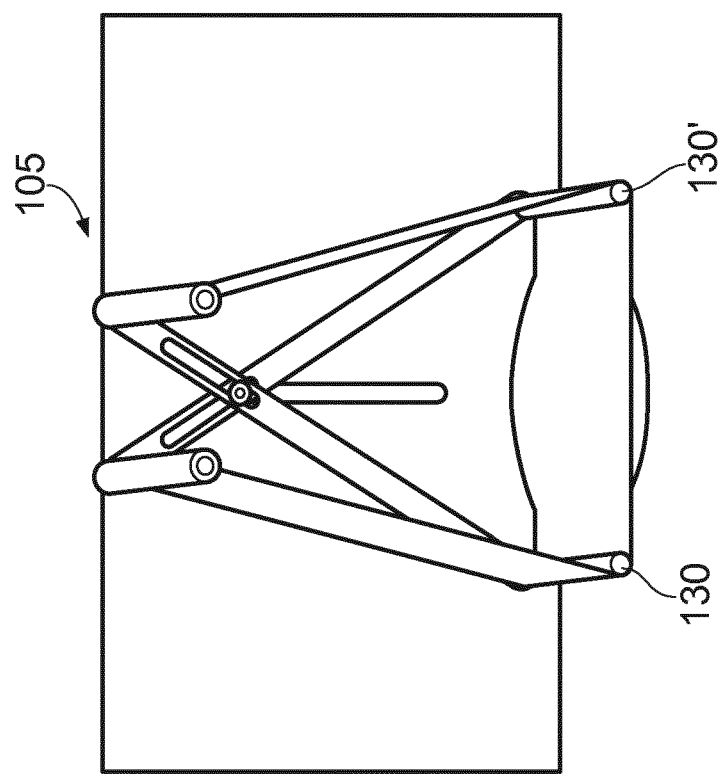
Figure 14:
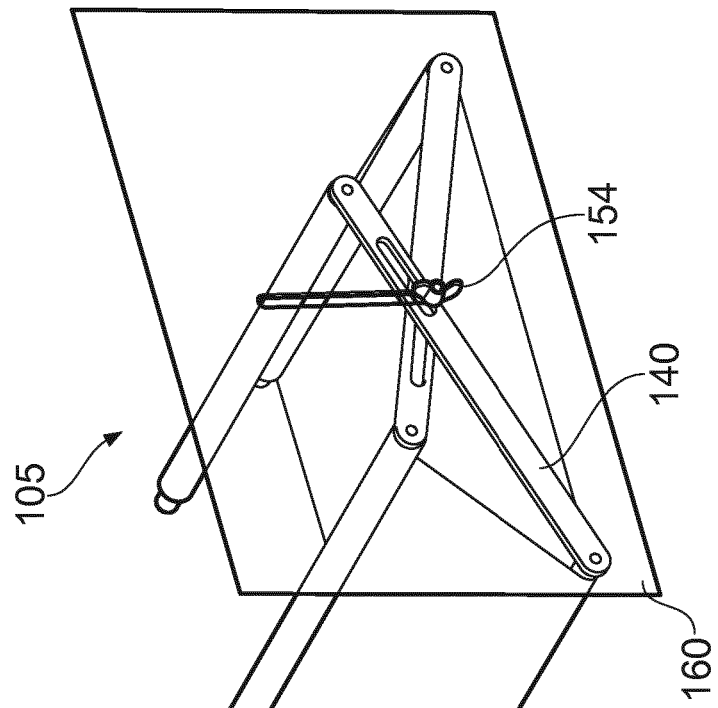
Figure 13:
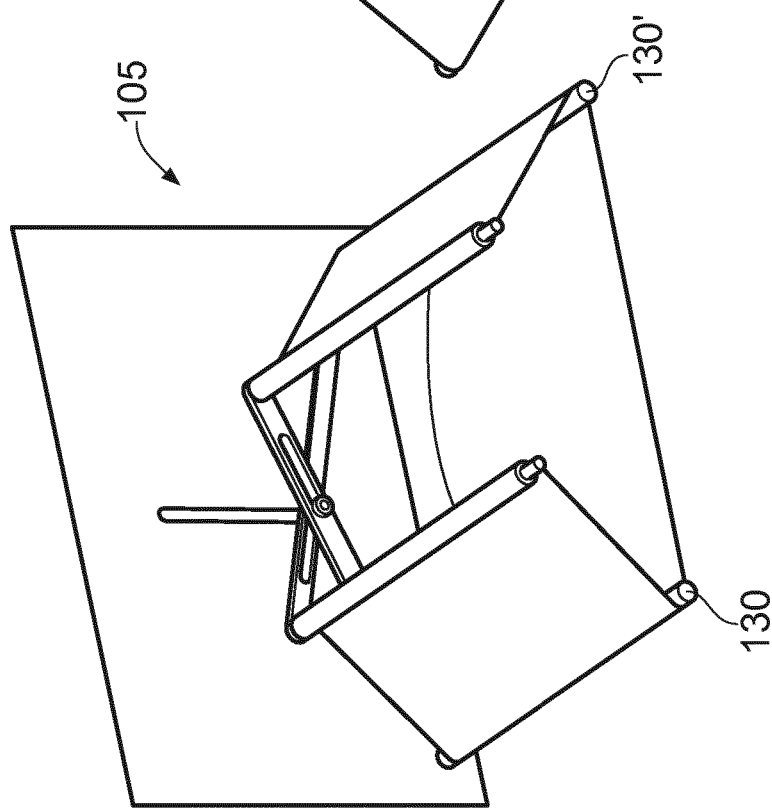

FIGS. 11 and 12 show the apparatus 105 in an initial position with the smallest distance between the rollers 130/130'. FIGS. 13 and 14 shows the apparatus 105 in its final position with the mechanism allowing the maximum distance between the rollers, and thereby allowing additional volume in the tube for cell culture. Manual adjustments can be made according to a predetermined table, or manually in response to increased cell density measured via said sample port 12*c*.

The invention is not to be seen as limited by the embodiments described above, but can be varied within the scope of the appended claims as is readily apparent to the person skilled in the art. For instance, other tube holders could be employed, for example opposed pinch rollers, or resiliently urged features other than the jaws described above could be used. Stepper motor 42 could be replaced with an electrical motor of a different type, or a non-electrically powered actuator, for example a pneumatic actuator. Moreover the first embodiment can be made manually powered, and the second embodiment can be made automatic. One significant features of the embodiments shown is that the fluid tight sealing is brought about by folding of the tube material, i.e. bending the tube material by 90 degrees or more, which contributes to a sealing effect.

The invention claimed is:

1. A cell culture apparatus comprising:
   a cell culture container comprising a flexible tube;
   a support table; and
   a pair of opposed holders for opposed portions of the flexible tube and for holding a central portion of the flexible tube in a fluid tight manner such that fluid is inhibited from passing toward the opposed portions of the flexible tube inside the pair of opposed holders from the central portion, the spacing between the pair of opposed holders being adjustable to provide an adjustable sealed volume in the central portion of the flexible tube between the pair of opposed holders,
   wherein each opposed portion of the opposed portions of the flexible tube is a rolled tube portion comprising at least one roll or a folded tube portion comprising at least one fold within a respective holder of the pair of opposed holders, and
   wherein each holder of the pair of opposed holders is hinged.

2. The cell culture apparatus as claimed in claim 1 wherein, the culture container includes plural fluid ports located between the pair of opposed holders when the container is mounted on the support table.

3. The cell culture apparatus as claimed in claim 1, wherein, each opposed portion of the flexible tube comprises the folded tube portion.

4. A cell culture apparatus as claimed in claim 1, wherein, the cell culture apparatus is controlled using a feedback mechanism.

5. The cell culture apparatus of claim 1, wherein each holder of the pair of opposed holders comprises two jaws defining a circuitous path between the two jaws, and wherein the tube is folded in the folded tube portion within the circuitous path.

6. The cell culture apparatus of claim 5, wherein the circuitous path defines a fold of more than 90 degrees.

7. The cell culture apparatus of claim 1, wherein an unfolded or unrolled portion of the flexible tube between the pair of opposed holders comprises access ports.

8. The cell culture apparatus of claim 1, wherein each opposed portion of the opposed portions of the flexible tube is rolled into at least one roll in the rolled tube portion within the respective holder of the pair of opposed holders.

9. The cell culture apparatus of claim 1, wherein each holder of the pair of opposed holders comprises two jaws coupled by a hinge pin.

10. The cell culture apparatus of claim 1, wherein each holder of the pair of opposed holders comprises secures a respective end of the flexible tube.

11. The cell culture apparatus of claim 1, wherein each holder of the pair of opposed holders comprises two jaws forming a cavity, and wherein a folded and pleated respective end of each tube is held within the respective cavity of the respective holder.

12. The cell culture apparatus of claim 1, wherein each opposed portion of the opposed portions is a folded tube portion comprising a folded and pleated end of the tube held within a respective holder of the opposed holders.

* * * * *